United States Patent [19]

Numata et al.

[11] Patent Number: 5,264,567
[45] Date of Patent: Nov. 23, 1993

[54] GM₃ ANALOGOUS COMPOUND

[75] Inventors: Masaaki Numata, Kawagoe; Mamoru Sugimoto, Tokyo; Shuji Fujita, Tachikawa; Masanori Kobayashiu; Kenkichi Tomita, both of Tokyo; Makoto Tanaka, Koshigaya; Tomoya Ogawa, Musashino, all of Japan

[73] Assignee: Mect Corporation, Tokyo, Japan

[21] Appl. No.: 13,993

[22] Filed: Feb. 5, 1993

Related U.S. Application Data

[63] Continuation of Ser. No. 779,992, Oct. 21, 1991, abandoned.

Foreign Application Priority Data

[30]

Oct. 22, 1990 [JP] Japan ................................ 2-283661

[51] Int. Cl.⁵ ..................... C07G 17/00; C07H 1/00; C07H 5/04; A01N 43/04
[52] U.S. Cl. .................................. 536/53; 536/1.11; 536/55.1; 536/124; 536/123.1
[58] Field of Search ................. 536/53, 1.1, 55.1, 124, 536/18.7, 17, 55.3, 121, 122; 514/54

[56] References Cited

U.S. PATENT DOCUMENTS 4,918,170 4/1990 Hasegawa et al. ................... 536/1.1
4,950,750 8/1990 Ogawa et al. ....................... 536/18.7
4,968,786 11/1990 Ogawa et al. ....................... 536/17.9

Primary Examiner—Michael G. Wityshyn
Assistant Examiner—Louise N. Leary
Attorney, Agent, or Firm—Burns, Doane, Swecker and Mathis

[57] ABSTRACT

GM₃ analogous compound (I) below:

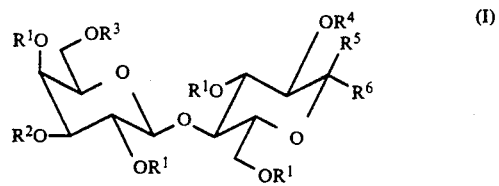

wherein one of $R^2$ and $R^3$ represents a neuramic acid group represented by general formula (V):

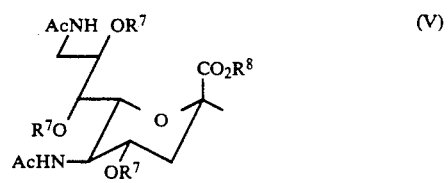

$R^5$ represents

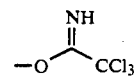

or hydrogen; $R^6$ represents hydrogen or a ceramide group represented by general formula (VI):

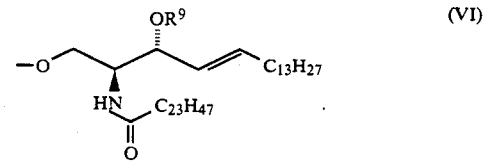

6 Claims, No Drawings

GM₃ ANALOGOUS COMPOUND

This application is a continuation of application Ser. No. 07/779,992 filed Oct. 21, 1991, now abandoned.

BACKGROUND OF THE INVENTION

1. Filed of the Invention

The present invention relates to GM₃ analogous compounds and a process for preparing the compounds. More particularly, the present invention relates to GM₃ analogous compounds exhibiting higher stability and usable as a cancer antigen, and intermediates thereof.

2. Description of the Related Art

Glycolipids found in mammal cells are glycosides between ceramides, which are sphingosines (long chain amino alcohols) to which aliphatic acids have been attached through an amide linkage, and one or more sugars such as glucose, galactose, N-acetyl glucosamine, N-acetyl galacotosamine, fucose, sialic acid, etc. Among these glycosides, those containing sialic acid are called gangliosides.

Gangliosides exsit mainly in the outer leaflet of the bilayer of the mammal cell membrane. Recent studies show that gangliosides play important roles in reception and recognition of, and response to, information in cells, receptor mechanism, differentiation, cell propagation, malignant cell transformation, cell behavior, etc.

It has been known that the ganglioside GM₃, one of the above-mentioned gangliosides, closely relates to differentiation of intestinal tissue and contact inhibition of cell growth. It has been also known that the growth of fibroblast of baby hamsters in the presence of fibroblast factor is specifically inhibited by the presence of ganglioside GM₃ added from the outside. Further, ganglioside GM₃ has been detected in the natural melanoma cells as a tumer associated antigen.

Recently, by using the gangliosides, preparation of a monoclonal antibody recognizeing the oligosuccharides and pharmaceutical preparations having the biological activity thereof have been developed (see Japanese Patent Disclosure Nos. 63-301796 and 1-132374 (JP-A-301796/1988 and JP-A-132374/1989).

At the preparation of a monoclonal antibody by using ganglioside 9-O-acetyl GM₃ as the antigen, the low chemical stabiltiy of ganglioside 9-O-acetyl GM₃ is a problem. That is, since the chemical stabiltiy of ganglioside 9-O-acetyl GM₃ is low, it was hard to prepare a monoclonal antibody to ganglioside 9-O-acetyl GM₃.

SUMMARY OF THE INVENTION

An object of the presnet invention is to provide a novel ganglioside 9-N-acetyl GM₃ which is analogous to ganglioside 9-O-acetyl GM₃ and exhibits higher stability. More particularly, an object of the invention is to provide a GM₃ analogous compound in which O-Ac (O-Acetyl group) at the 9-position of the natural GM₃ is converted into N-Ac (N-acetyl group) and which is analogous to the natural GM₃ and has the high chemical stability.

The present invention relates to compounds represented by general formula (I) below:

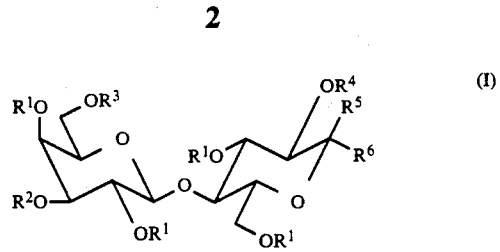

wherein $R^1$ represents hydrogen or an acetyl group; one of $R^2$ and $R^3$ represents a nueraminic acid group represented by general formula:

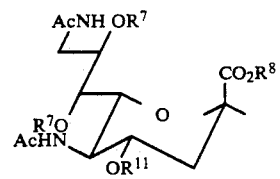

wherein $R^7$ represents hydrogen or an acetyl group, $R^8$ represents a methyl group or sodium, and Ac means an acetyl group; the other represents hydrogen or an acetyl group; $R^4$ represents hydrogen or a pivaloyl group; $R^5$ represents

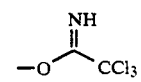

or hydrogen; $R^6$ represents hydrogen or a ceramide group represented by general formula:

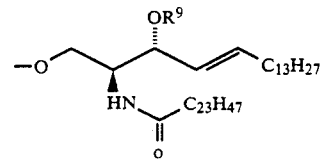

wherein $R^9$ represents hydrogen or a benzoyl group; provided that when $R^5$ is

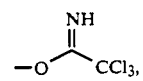

$R^6$ is hydrogen or when $R^5$ is hydrogen, $R^6$ represents the above ceramide group.

Further the present invention relates to intermediates represented by general formula (II) below:

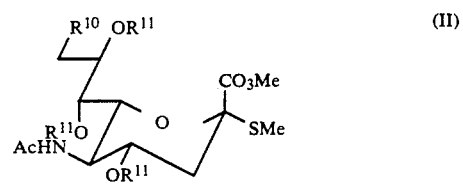

wherein $R^{10}$ represents $N_3$ or OMs and $R^{11}$ represents hydrogen or an acetyl group.

Further the present invention relates to a process for preparation of intermediate compounds represented by the formual (IV):

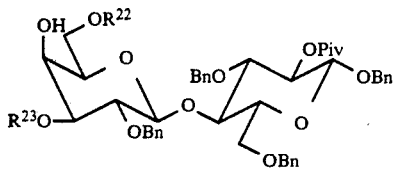

wherein one of $R^{22}$ and $R^{23}$ represents a neuraminic acid group:

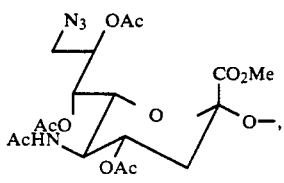

the other represents a benzyl group, Bn means a benzyl group and Piv means a pivaloyl group; comprising reaction of a nueraminic acid derivative represented by general formula (II) below:

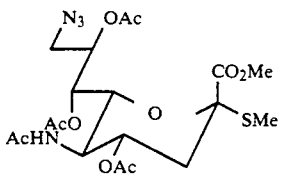

with t compound represented by general formula (III) below:

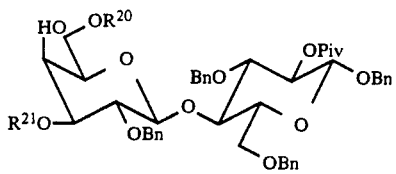

wherein one of $R^{20}$ and $R^{21}$ represents hydrogen and the othe represents a benzyl group, Bn means a benzyl group and Piv means a pivaloyl group; in the presence of a promoter. The compounds represented by general formula (IV) are intermediates of compounds represented by general formula (I) of the present invention.

Further, the present invention relates to compounds represented by general formula (V):

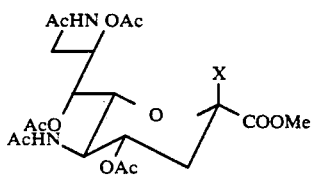

wherein X represents a halogen atom such as fluorine or chlorine. The compounds represented by formula (V) are intermediates of compounds represented by general formula (I) of the present invention.

The present invention will be explained in accordance with schemes 1, 2 and 3. Scheme 1 illustrates compounds represented by general formula (I) wherein $R^2$ is a nueraminic acid group represented by general formula (V) such as compounds (1), (2) and (3) and intermediates thereof. Scheme 2 illustrates compounds represented by general formula (I) wherein $R^3$ is a neuraminic acid group represented by general formula (V) such as compounds (4), (5) and (6) and intermediates thereof. Scheme 3 illustrates a systhesis pathway of compound (17) which is a starting material of compounds represented by formula (I) through the intermediates represented by general formula (V).

In this specification, Ac means an acetyl group, Me means a methyl group, piv means a pivaloyl group, Bn means a benzyl group, Bz means a benzoyl group and Ms means a methanesulfonyl group.

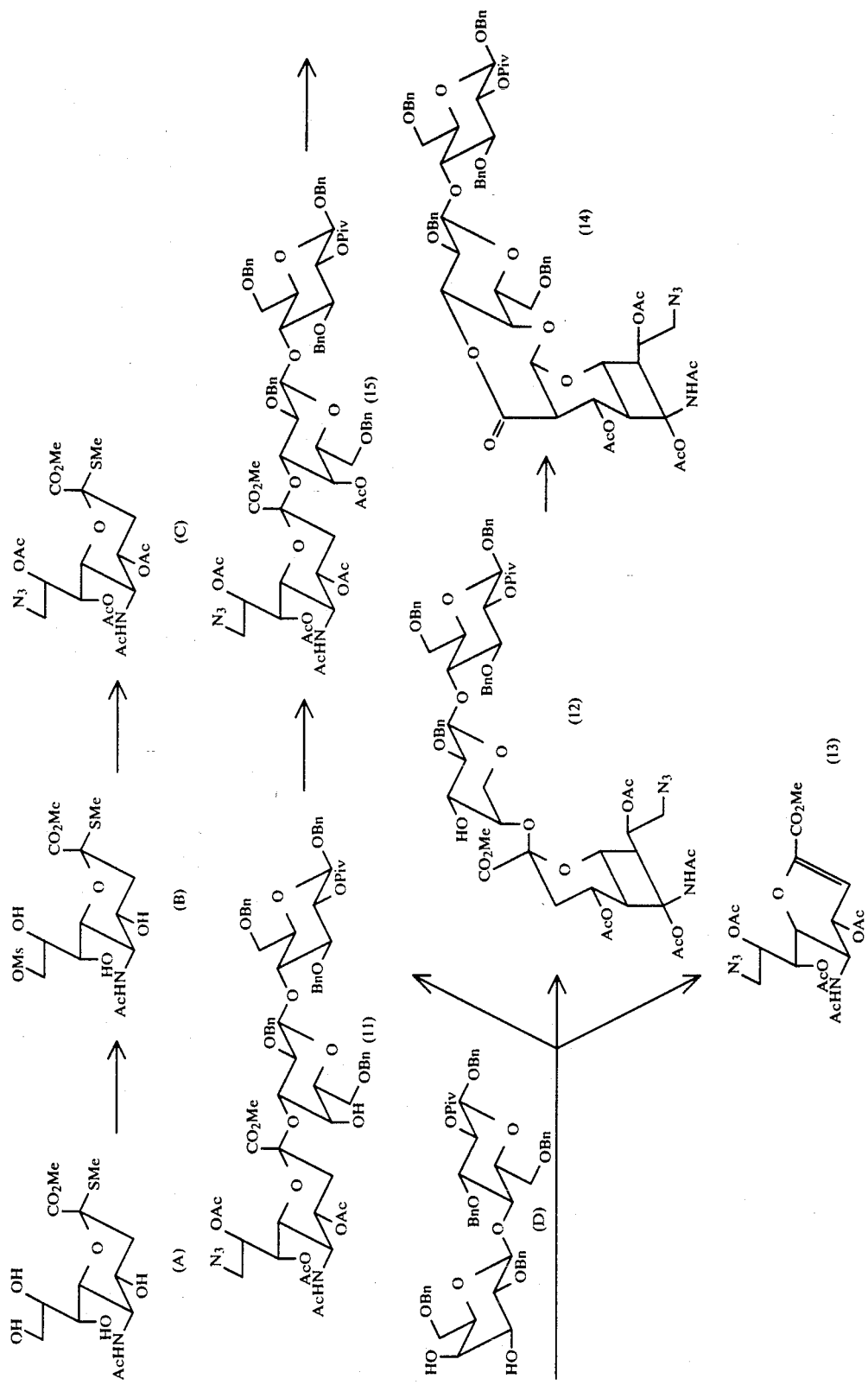

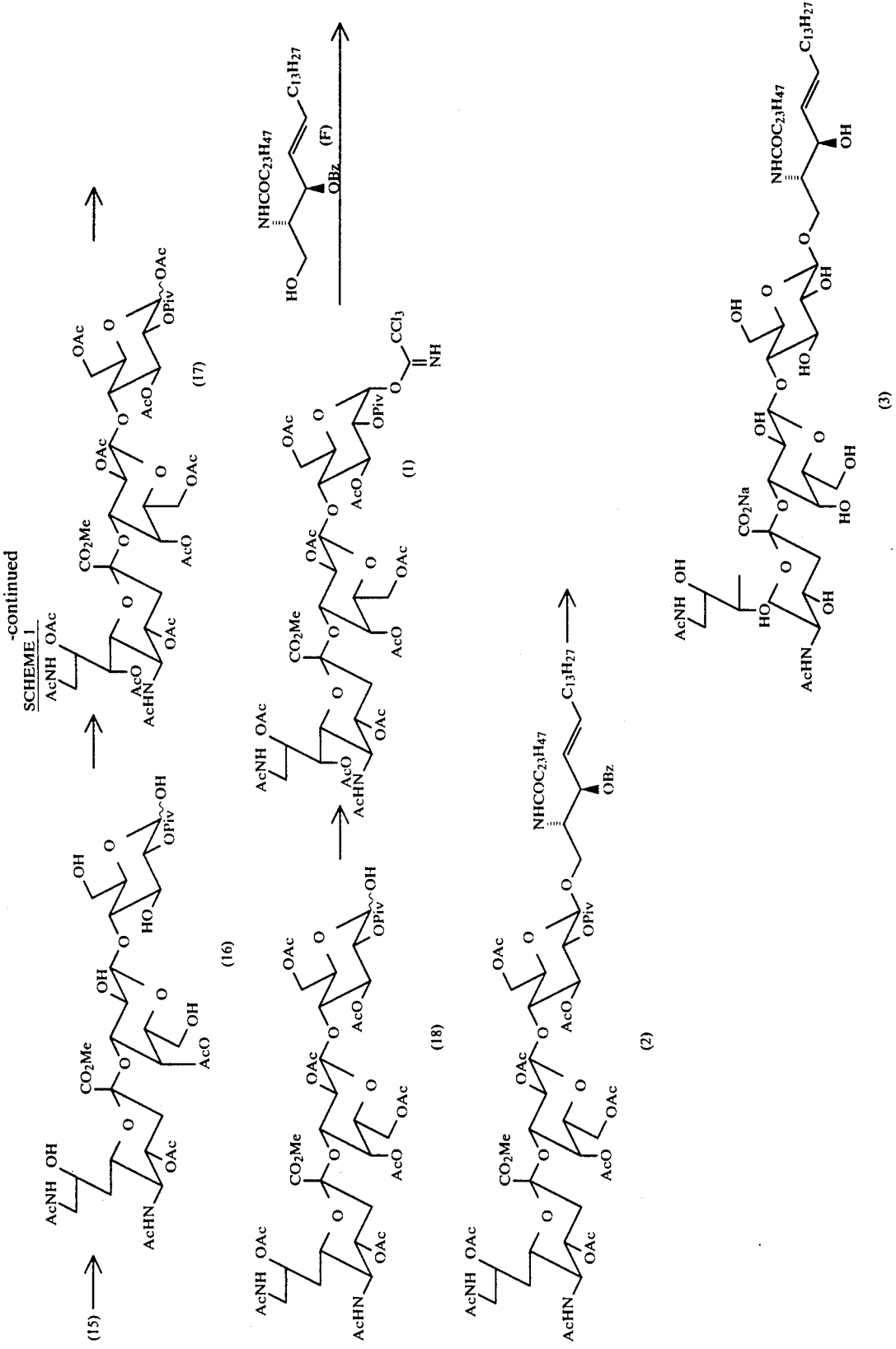

SCHEME 2
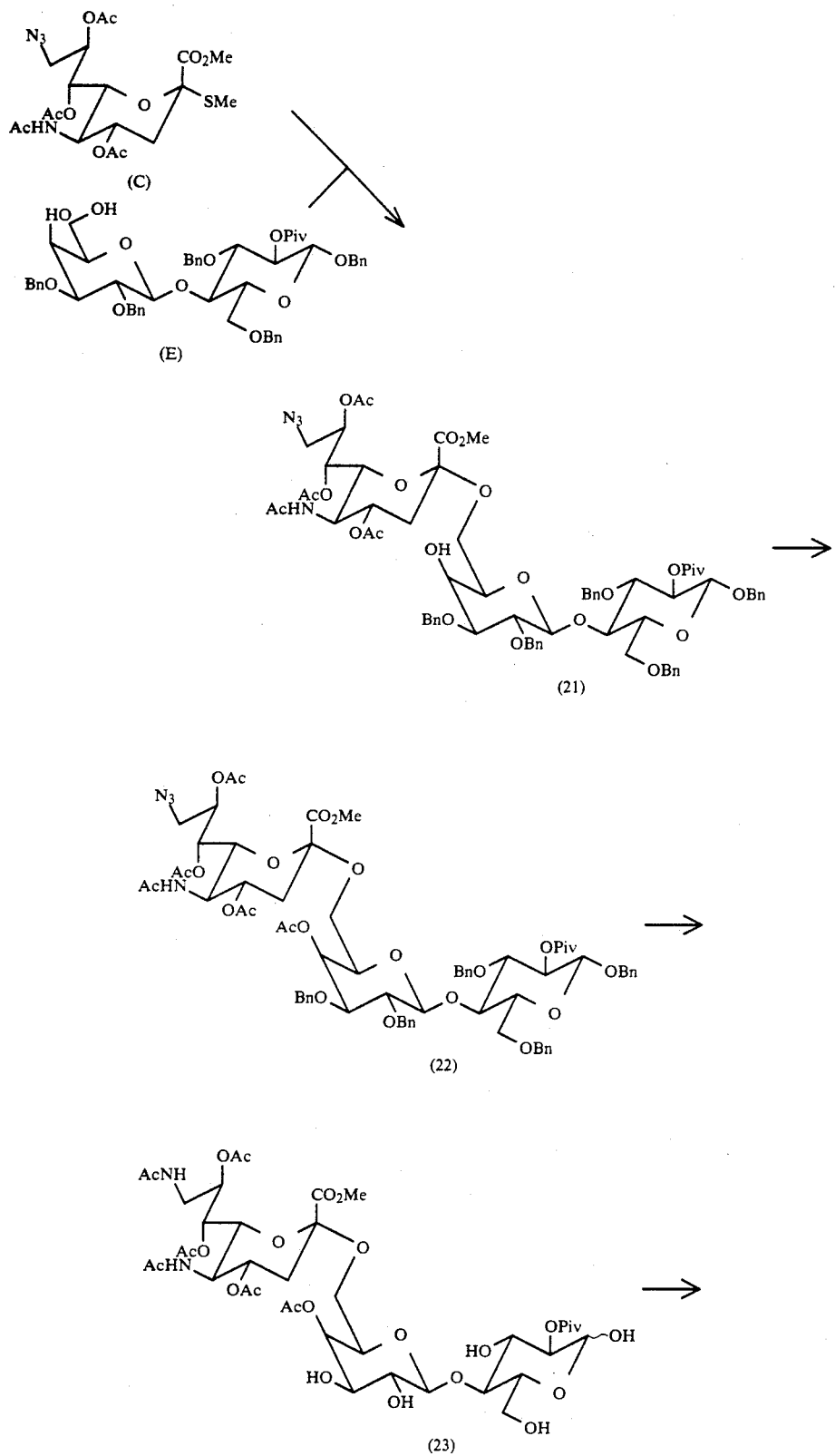

SCHEME 2
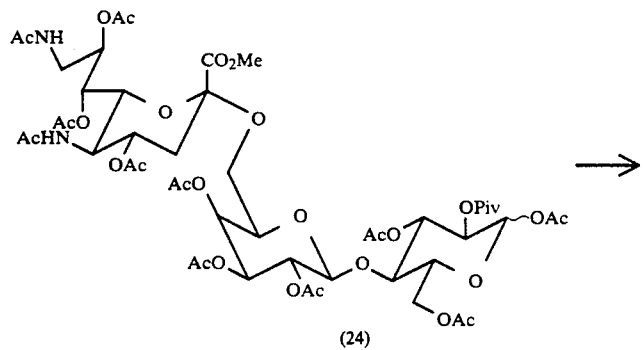
(24)
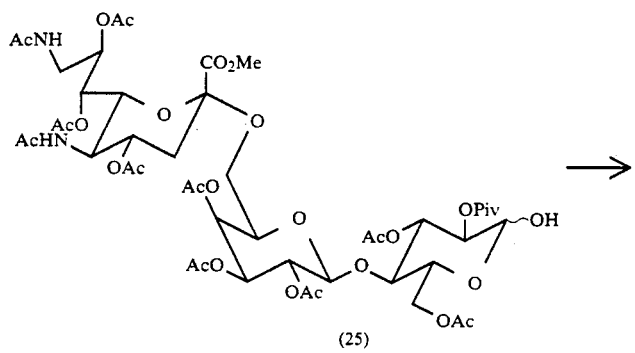
(25)
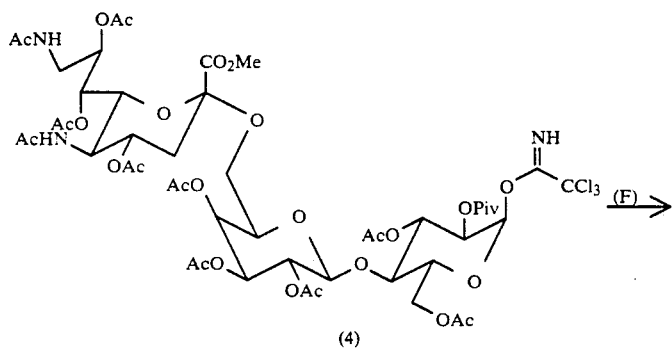
(4)
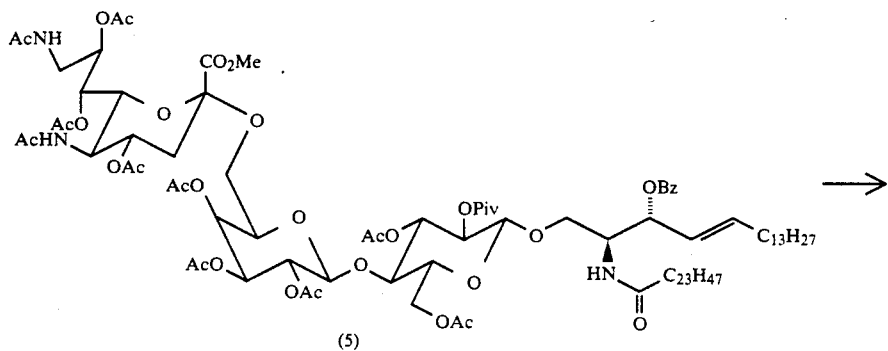
(5)

-continued
SCHEME 2
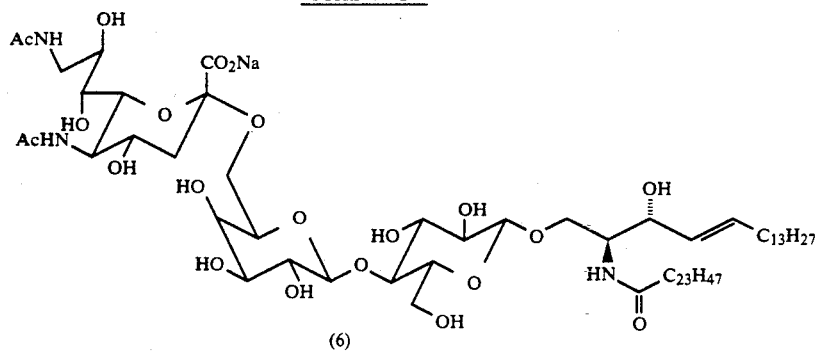

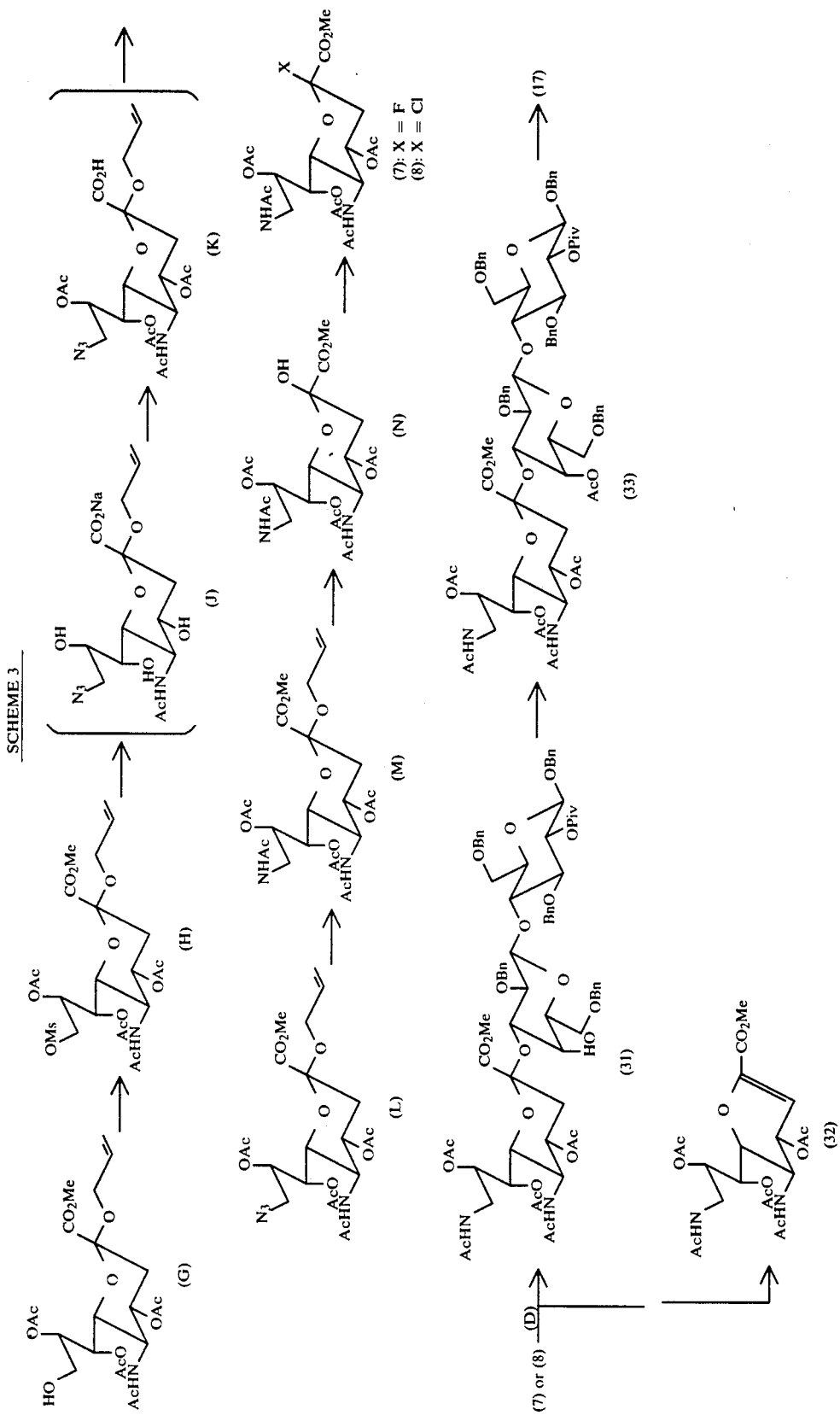

Reactions shown in scheme 1 will be explained below:

Starting compound (A) is a known compound and can be prapared in accordance with the method reported in Shuji Fujita, Tomoya Ogawa et al, Japan Society for Bioscience, Biotechnology, and Agrichemistry 1990, p391. The disclosure of which is hereby incorporated by reference.

Compound (B) is obtained by reaction of compound (A) with methanesulfonyl chloride ($MeSO_2Cl$). This reaction can be conducted, for example, in a solvent such as pyridine or the like, at a tempretaure between $-40°$ and $40°$ C. for 0.5 to 12 hours.

Coumpound (C) is obtained by reaction of compound (B) with sodium azide. This reaction can be carried out, for example, in a solvent such as N,N-dimethylformamide (DMF) or the like at a temperature of from $60°$ to $150°$ C. for 1 to 24 hours.

Compound (11) is obtained by reaction of compound (C) with compound (D). At the reaction, compounds (12) and (13) are also produced and compound (12) is converted into compound (14) at room temperature. Compound (D) is a known compound and can be prepared in accordance with the method reported in Japanese Patent Disclosure No. 1-290689 (=JP-A-290689/1989). The disclosure of which is hereby incorporated by reference.

The reaction of compound (C) with compound (D) is conducted in the presence of a glycosyl catalyst. Examples of the glycosyl catalyst include AgOTf-PhSeCl-TMSOTf (trimethylsilyltrifluoromethane sulfonate), AgOTf-PhSeCl and DMTST (dimethyl(methylthio)-sulfonium trifluorate) or the like. At the reaction, a dehydrating agent such as Molecular Sieve (MS)-4A, MS-4A-MS-3A or the like can be presented. The reaction is suitably conducted in the presence of a solvent such as carbon tetrachloride, acetonitrile-dichloromethane, dichloromethane, acetonitrile, chloroform, toluene, tetrahydrofuran (THF), benzene, 1,2-dichloroethane or the like. The reaction temperature is suitably controlled at $-78°$ to $20°$ C. and the reaction period is suitably between 10 minutes and 24 hours.

Compound (15). is obtained by acetylation of compound (11) with acetic anhydride in the presence of a catalyst such as 4-dimethylaminopyridine or the like. This reaction can be conducted with acetyl chloride in place of acetic anhydride. The reaction is carried out in a solvent such as pyridine, THF, DMF or the like at a temperature of from $0°$ to $60°$ C. for 1 to 24 hours.

Compound (16) is obtained by catalytic reduction of compound (15). A catalyst such as Pd-C, $Pd(OH)_2$, $PtO_2$, $Pd-C/Ac_2O$, $PdCl_2$—NaOAc, Lindlar catalyst or the like under hydrogen atomsphore can be used for the reduction. A solvent such as methanol, ethanol, PrOH (propyl alcohol), acetic acid or the like can be used for the reduction. The reaction temperature suitably ranges from $10°$ to $60°$ C. and the reaction period suitably ranges from 1 to 48 hours.

Compound (17) is obtained by acetylation of compound (16). The reaction conditions can be the same as those of the acetylation of compound (11).

Compound (18) is obtained by regioselective elimination of an acetyl group of compound (17) by hydradine-acetic acid ($H_2NNH_2 \cdot AcOH$) or piperidine-AcOH in the presence of a solvent such as DMF or the like. The reaction temperature suitably ranges from $20°$ to $100°$ C. and the reaction period suitably ranges from 1 minute to 12 hours.

Compound (1) of the present invention is obtained by reaction of compound (18) with trichloroacetonitrile ($CCl_3CN$) in the presence of a catalyst. 1,8-diazabicyclo[5.4.0]-7-undecene (DBU), NaH, LiH, $K_2CO_3$ or the like can be used as the catalyst. The reaction can be conducted in a solvent such as 1,2-dichloroethane, dichloromethane, toluene, THF or the like at a temperature of from $-40°$ to $50°$ C. for 1 to 24 hours.

Compound (2) is obtained by reaction of compound (1) with benzoylceramide (F) which is a known compound and prepared in accordance with the method described in Japanese Patent Disclosrue No. 61-282393 (JP-A-282393/1986). The reaction is suitably carried out in the presence of a catalyst such as $BF_3 \cdot Et_2O$, TMSOTf or the like desiccating agent sucn as MS-4A, MS-AW-300 or the like. Chloroform, THF, dichloromethane, 1,2-dichloroethane, toluene, benzene, acetonitrile or the like can be used as a solvent, and the reaction is conducted at a temperature of from $-40°$ to $50°$ C. for 1 to 24 hours.

Compound (3) is obtained by elimination of protective groups such as actyl groups, pivaloyl groups, benzoyl groups and methylesters. The elimination of the protective groups is carried out by reacting compound (2) with NaOMe, NaOH, KOH, LiOH, $K_2CO_3$ or the like in a solvent such as methanol or a mixed solvent such as methanol-THF, methanol-dioxane or methanol-chloroform. The reaction temperature is suitably from $0°$ to $50°$ C. and the reaction period suitably ranges from 0.5 to 24 hours.

Reactions shown in scheme 2 will be explained below:

Compound (21) is obtained by reaction of compound (C) with compound (E). This reaction can be conducted under the same conditions as those of the reaction between compounds (C) and (D). At the reaction, compound (13) is also produced.

Compound (E) is prepared from a known compound by the method reported in Tetrahedron Letters. Vol.29 (33), p4097–4100, 1988.

Compound (22) is obtained by acetylation of compound (21). This acetylation can be carried out under the same conditions as those of the acetylation of compound (11).

Compound (23) is obtained by catalytic reduction of compound (22). This catalytic reduction can be conducted under the same conditions as those of the catalytic reduction of compound (15).

Compound (24) is obtained by acetylation of compound (23). This acetylation can be conducted under the same conditions as those of the acetylation of compound (11).

Compound (25) is obtained by selective elimination of an acetyl group of compound (24). This elimination can be conducted under the same conditions as those of the reaction of compound (17) to compound (18).

Compound (4) of the present invention is obtained by reaction of compound (25) with trichloroacetonitrile This reaction can be conducted under the same conditions as those of the reaction of compound (18) with trichloroacetonitrile.

Compound (5) is Obtained by reaction of compound (4) with benzoylceramide (F) and compound (6) is obtained by elimination of protective groups of compound (5). The reaction of compound (4) with the benzoylceramide can be conducted under the same conditions as those of the reaction of compound (1) with the benzoylceramide. The elimination reaction of protective groups can be conducted under the same conditions as those of the elimination reaction of compound (2).

Compound (17) can be prepared in accordance with scheme 3 from known compound (G) obtainable according to Japanese Patent Disclosure No. 63-14792 (JP-A-14792/1988).

Compound (H) is obtained by reaction of compound (G) with methanesulfonyl chloride (MeSO₂Cl). This reaction is conducted in a solvent such as pyridine or the like at a temperature of from −40° to 40° C. for 0.5 to 12 hours.

Compound (J) is obtained by reaction of compound (H) with sodium azide. This reacion can be conducted in a solvent such as N,N-dimethylformamide (DMF) or the like at a temperature of from 60° to 150° C. for 1 to 24 hours.

Compound (K) is obtained by acetylation of compound (J) with acetic anhydride in the presence of a catalyst such as 4-dimethylaminopyridine. This reaction can be conducted with acetyl chloride in place of acetic anhydride. The reaction can be carried out in a solvent such as pyridine, THF, DMF or the like at a temperature of from 0° to 60° C. for 1 to 24 hours.

Compound (L) is obtained by esterification of compound (K) with diazomethane.

Compound (M) is obtained by reaction of compound (L) with Ph₃P-H₂O, Bu₃P-H₂O in benzene or H₂S in a solvent such as pyridine, THF, DMF or the like at a temperature of from 0° to 60° C. for 1 to 24 hours followed by acetylation of the product with acetic anhydride or acetyl chloride.

Compound (N) is obtained by catalytic reduction of compound (M). The reduction can be conducted by use of a catalyst such as Pd-C, PdCl₂-NaOAc, [Ir(COD)(-PMePh₂)₂] PF₆ or the like under hydrogen atomsphore in a solvent such as methanol, ethanol, THF, acetic acid or the like at a temperature of from 0° to 100° C. for 1 to 24 hours.

Compound (7) is obtained by reaction of compound (N) with diethylaminosulfur trifluoride. This reaction can be conducted in a solvent such as 1,2-dichloroethane, toluene, CHCl₃, THF or the like at a temperature of from −60° to 60° C. for 10 minutes to 5 hours.

Also compound (8) is obtained by reaction of compound (N) with hydrogen chloride gas or Vilsmeyer's agent. This reaction can be conducted in a solvent such as 1,2-dichloroethane, AcCl, THF, toluene or the like at a temperature of from −20° to 40° C. for 1 to 24 hours.

Compound (31) is obtained by reaction of compound (D) with compound (7) or (8). At the reaction, compound (32) is also produced. The reaction of compound (D) with compound (7) or (8) is conducted in the presence of a glycosyl catalyst. Examples of the glycosyl catalyst include AgOTf-PhSeCl-TMSOTf (trimethylsilyltrifluoromethane sulfonate), AgOTf-PhSeCl, DMTST (dimethyl(methylthio) sulfonium trifluorate) and the like. At the reaction, a desiccating agent such as Molecular Sieve (MS)-4A, MS-4A-MS-3A or the like can be presented. This reaction is suitably conducted in a solvent such as carbon tetrachloride, acetonitrile-dichloromethane, dichloromethane, acetonitrile, trichloromethane, toluene, tetrahydrofuran (THF), benzene, 1,2-dichloroethane or the like. The reaction temperature suitably ranges from −78° to 20° C. and the reaction period suitalby ranges from 10 minutes to 24 hours.

Compound (33) is obtained by acetylation of compound (31) with acetic anhydride or acetyl chloride. This reaction can be conducted in a solvent such as pyridie, THF, DMF or the like at 0° to 60° C. for 1 to 24 hours.

Compound (17) is obtained by catalytic reduction of compound (33) followed by acetylation of the reduced product. The reduction is conducted in the presence of a catalyst such as Pd-C, Pd(OH)₂, PtO₂, Pd-C/Ac₂O, PdCl₂—NaOAc, Lindlar catalyst or the like in a solvent such as methanol, ethanol, propanol, acetic acid or the like at a temperature of from 10° to 60° C. for 1 to 48 hours. The acetylation can be conducted under the same conditions as those of the acetylation of compound (31).

USEFULNESS OF THE INVENTION

Compounds (1) to (6) are novel compounds. Among them, compounds (3) and (6) are GM₃ having N-acetyl group at the 9-position (9-N-Ac) which are more stable than the natural GM₃ having O-acetyl group at the 9-position (9-O-Ac) and are expected to be useful for diagnosis and therapy of cancer. Further, since 9-O-Ac-GM₃ is known to work as a receptor of influenza virus, it is expected that 9-N-Ac type compounds (3) and (6) will be able to be applied in the field of virus infection.

Compounds (B), (C), (7) and (8) are also novel comounds and are useful as intermediates of compounds (1) to (6).

The present invention will be set forth more in detail in refernce to the following examples.

EXAMPLES

Example 1

Compound (A)→(B)

50 mg (0.145 mmol) of compound (A) was dissolved in 2 ml of pyridine. 16.6 mg (0.145 mmol) of methanesulfonyl chloride was added to the pyridine solution under cooling at −20° C. and stirred for 1.5 hours under the same conditions. The reaction solution was purified by silica gel column chromatography (C-300, 25 g, CHCl₃:MeOH=8:1) to obtain 60 mg of compound (B) (yield: 99%).

$R_f$=0.388 (CHCl₃:MeOH=6:1)

500 MHz ¹H-NMR (CDCl₃, TMS) δH; 1.928(t, 1H, J=12.8 Hz, H-3ax) 2.081 (s 3H NAc) 2.132 (s, 3H, SCH₃), 2.868 (dd, 1H, J=4.8, 13.2 Hz, H-3eq), 3.074 (s, 3H, SO₂CH₃), 3.309 (d, 1H, J=10.3Hz, H-6), 3.542 (d, 1H, J=9.9Hz, H-7), 3.653 (dt, 1H, J=4.8, 10.3Hz, H-4), 3.849 (s, 3H, OCH₃), 4.114 (br, 1H, H-8), 4.442 (dd, 1H, J=5.1, 11.0Hz, H-9′),4.564 (dd, 1H, J=1.8, 10.6Hz, H-9), 5.944(d,1H, J=8.1Hz, NH)

Example 2

Compound (B)→(C)

3.716 g (7.365 mmol) of compound (B) was dissolved in 60 ml of dimethylformamide. 1.606 g (6.826 mmol) of sodium azide was added to the dimethylformamide solution and stirred overnight at 110° C. The reaction solution was evaporated to dryness and the residue was dissolved in a mixture of pyridine 10 ml and acetic anhydride 10 ml. 175 mg of 4-dimethylaminopyridine was added to the mixture and stirred overnight at room temperature. The reaction solution was evaporated to dryness and the residue was dissolved in chloroform. Then the chloroform solution was washed with diluted hydrochloric acid and saturated saline solution, and dried over anhydrous magnesium sulfate. The dried solution was evaporated to dryness and the residue was treated with diazomethane. The residue was purifed by silica gel column chromatography (C-300, 600 g, toluene: ethyl acetate=1:2) to obtain 2.715 g of compound (C) (yield: 62.5%).

Rf=0.275 (toulene:ethyl acetate=1:2)

$[\alpha]_D$ 33.6° (C=0.1, CHCl$_3$)

500 MHz $^1$H-NMR (CDCl$_3$, TMS) δH; 1.881(s, 3H, CH$_3$), 1.991(t, 1H, J=12.5Hz, H-3ax), 2.033, 2.122, 2.163, 2.190 (4S, 12H, CH$_3$), 2.739 (dd, 1H, J=4.4, 12.5Hz, H-3eq), 3.266 (dd, 1H, J=5.5, 13.6Hz, H-9'), 3.649 (dd, 1H, J=2.9, 13.6Hz, H-9), 3.827(s, 3H, OCH$_3$), 4.083 (q, 1H, J=10.6Hz, H-5), 4.876 (td, 1H, J=10.3, 4.4Hz, H-4), 5.130 (d, 1H, J=10.3Hz, NH), 5.296 (ddd, 1H, J=3 3, 5.9, 7.3Hz, H-8), 5.340 (dd, J=2 2, 7.3Hz, H-7)

Elementary analysis C$_{19}$H$_{28}$N$_4$O$_{10}$S$_1$ ⅛ CH$_3$C$_6$H$_5$

Calculation: C 46.26 H 5.66 N 10.86

Found: C 45.96 H 5.66 N 11.01

Example 3

Compounds (C)+(D)→(11)

150 mg (0.297 mmol) of compound (C), 522 mg (0.595 mmol) of compound (D) and 3 ml of acetonitrile were added to 300 mg of activated Molecular Sieve 3A and 300 mg of activated Molecular Sieve 4A, and stirred at 20° C. for 1 hour. 114.8 mg (0.447 mmol) of AgOTF dissolved in 1 ml of acetonitrile and 85.5 mg (0.462 mmol) of PhSeCl dissolved in 1 ml of acetonitrile were added to the above reaction solutoin at −10° C. and stirred for 20 hours under the same conditions. The reaction solution was diluted with chlorofrom and filtered with Celite. The filtrate was washed with an aqueous sodium hydrogen carbonate solution, saturated saline solution and dried over anhydrous magnesium sulfate. The dried solution was distilled under reduced pressure. The residue was purified by silica gel column chromatography (C-300, 20 g, toluene:ethyl acetate=2:3 and 3:2) and purified by Lobar ® column (LiChroprep Si60, toluene:methanol=9:1) to obtain 131 mg of compound (11) (yield: 33%). Compounds (12) and (13) were also obtained.

Rf=0.219 (toluene:methanol=9:1)

$[\alpha]_D$ −12.2° (C=1.3, CHCl$_3$)

500 MHz $^1$H-NMR (CDCl$_3$, TMS) δH; 1.129(s, 9H, $^t$Bu), 1.870, 1.931, 2.017, 2.110, (4s, 12H, Ac), 2.520 (dd, 1H, J=4.7,11.9Hz, H-3ceq), 2.545 (d, 1H, J=2.9Hz, OH), 3.056 (dd, 1H, J=5.5, 13.6Hz, H-9c), 3.763 (s, 3H, OCH$_3$), 3.980 (dd, 1H, J=2.2, 11.0Hz, H-6c), 4.107 (q, 1H, J=10.3Hz, H-5c), 4.253, 4.334(2d, 2H, J=12.1Hz, CH$_2$Ph), 4.448 (d, 1H, J=7.7Hz, H-1a), 4.581 (d, 1H, J=12.9Hz, CH$_2$Ph), 4.697 (d,1H, J=12.1Hz, CH$_2$Ph), 4.763 (d, 1H, J=11.7Hz, CH$_2$Ph), 4.819 (m, 1H, H-4c), 4.852 (d, 1H, J=12.1Hz, CH$_2$Ph), 4.966 (d, 1H, J=11.0Hz, CH$_2$ Ph), 5.083 (d, 1H, J=10.3Hz, NH), 5.117 (dd, 1H, J=8.1, 9.2Hz, H-2a), 5.267 (m, 2H, H-7c, H-8c)

Elementary analysis C$_{70}$H$_{84}$N$_4$O$_{22}$ 1/5 CHCl$_3$

Calculatoion: C 62.12 H 6.25 N 4.13

Found: C 62.30 H 6.33 N 4.47

Compound (12): 26 mg (6.6%)

Rf=0. 344 (toluene:methanol=9:1)

500 MHz $^1$H-NMR (CDCl$_3$, TMS) δH; 1.154(s, 9H, $^t$Bu), 1.980, 2.070, 2.142 (3s, 9H, Ac), 3.635 (s, 3H, OCH$_3$), 3.963 (q, 1H, J=10.6Hz, H-5c), 4.799 (d, 1H, J=11.7Hz, CH$_2$Ph), 4.876 (d, 1H, J=12.5Hz, CH$_2$Ph), 4.914 (dt, J=4.4, 11.0Hz, 5.046 (6s, 1H, H-7c), 5.124 (dd, 1H, J=8.1, 9.2Hz, H-2a), 5.291 (m,1H, H-8c)

Compound (13): 72.4 mg (53.2%)

Rf=0.263 (toluene:ethyl acetate=1:2)

$[\alpha]^{22}_D$ 43.1° (C=0.8, CHCl$_3$)

500 MHz $^1$H-NMR (CDCl$_3$, TMS) δH; 1.929, 2.084, 2.100, 2.145 (4s, 12H, Ac), 3.477(dd, 1H, J=7.7, 13.6Hz, H-9'), 3.814(s, 3H, OCH$_3$), 3.885 (dd, 1H, J=2.9, 13.6Hz, H-9), 4.374(q, 1H, J=8.1Hz, H-5), 5.205 (td, 1H, J=3.3, 8.4Hz, H-8), 5.439 (d, 1H, J=8.8Hz, NH), 5.495 (t, 1H, J=3.3Hz, H-7), 5.530 (dd, 1H, J=2.9, 8.1Hz, H-4), 5.982 (d, 1H, J=2.9Hz, H-3)

Elementary analysis C$_{18}$H$_{24}$N$_4$O$_{10}$ ⅛ CH$_3$C$_6$H$_5$

Calculation: C 48.45 H 5.39 N 11.97

Found: C 48.40 H 5.44 N 11.11

Reference Example 1

Compound (11)→(15)

139 mg (0.210 mmol) of compound (11) was dissolved in a mixture of 2 ml of pyridine and 2 ml of acetic acid. 15 mg of 4-dimethylaminopyridine was added to the mixture and stirred at 20° C. for 18 hours. The reaction solution was evaporated to dryness and the residue was purified by silica gel column chromatography (C-300, 16 g, toluene:methanol= 9:1) and Sephadex LH-20 (methanol) to obtain 133.4 mg of compound (15) (yield: 93%).

Rf=0.390 (toluene:methanol=9:1)

$[\alpha]_D$ −19.5 (C=1.3, CHCl$_3$)

500 MHz $^1$H-NMR (CDCl$_3$, TMS) δH; 1.131(s, 9H, $^t$Bu), 1.836, 1.855, 1.989, 2.007, 2.099 5s, 15H, Ac), 2.533 (dd, 1H, J=4.8, 12.8Hz, H-3ceq), 3.067 (dd, 1H, J=6.6, 13.6Hz, H-9c), 3.453 (dd, 1H, J=7.7, 9.5Hz, H-2b), 3.837 (s, 3H, OCH$_3$), 4.092 (t, 1H, J=9.2Hz, H-4a), 4.115 (q, 1H, J=10.6Hz, H-5c), 4.159 (d, 1H, J=12.1Hz, CH$_2$ Ph), 4.315 (d, 1H, J=11.7Hz, CH$_2$ Ph), 4.321 (dd, 1H, J=3.7, 9.9Hz, H-3b), 4.434 (d, 1H, J=8.1Hz, H-1a), 4.562 (d, 1H, J=10.6Hz, CH$_2$ Ph), 4.580 (d, 1H, J=12.6Hz, CH$_2$ Ph), 4.594 (d, 1H, J=12.1Hz, CH$_2$ Ph), 4.678 (d, 1H, J=7.7Hz, H-1b), 4.842 (d, 1H, J=12.5Hz, CH$_2$ Ph), 4.876(d,1H, J=12.1Hz, CH$_2$ Ph), 4.937 (d, 1H, J=10.6Hz, CH$_2$ Ph), 5.047 (d,1H, J=3.3Hz, H-4b), 5.093 (d, 1H, J=10.6Hz, NH), 5.110 (dd, 1H, J=8.1, 9.5Hz, H-2a), 5.279(dd, 1H, J=2.6, 6.6Hz, H-7c), 5.395 (dt, 1H,J=2.9, 6.6Hz, H-8c)

Elementary analysis C$_{72}$H$_{86}$N$_4$O$_{23}$ 1/5 CHCl$_3$

Calculation C 61.97 H 6.21 N 4.00

Found C 61.98 H 6.21 N 4.31

Reference Example 2

Compound (15)→(16)→(17)

80.6 mg (58.5 μmol) of compound (15) was dissolved in 3 ml of methanol. 50 mg of 20% Pd(OH)$_2$ and 116 mg (1.136 mmol) of acetic anhydride was added to the methanol solution and catalytic reduction was conducted at 20° C. for 18 hours.

The reaction solution was filtered by Chromatodisc (25N, 0.45 μm) and evaporated to dryness. (Rf=0.679; ethyl acetate:ethanol:water=5:2:1, compound (16))

The residue was dissolved in a mixture of 2 ml of pyridine and 2 ml of acetic anhydride. 22 mg of 4-dimethylaminopyridine was added to the mixture and stirred at 20° C. for 20 hours. The reaction solution was evaporated to dryness and purified by silica gel column chromatography (C-300, 10 g, toluene:methanol=8:1) and Sephadex LH-20 (methanol) to obtain 60.7 mg of compound (17) (yield: 90%).

Rf=0.467 (chloroform:methanol=12:1)

$[\alpha]_D$ 2.51° (C=1.0, CHCl$_3$)

Compound (16)

500 MHz $^1$H-NMR (CD$_3$OD, TMS) δH; 1.223(s, 9H, $^t$Bu), 1.833, 1.916, 1.923, 1.982, 2.048, 2.060, 2.117, 2.119, 2.130 (9s, 18H, Ac), 2.619 (dd, 1H, J=4.4, 12.5Hz, H-3ceq), 3.839 (s, 3H, OCH$_3$), 5.029 (t, 1H, J=3.7Hz, H-4b), 5.201 (d, 1H, J=8.8Hz, H-7c), 5.225 (d, 0.6H, J=3.7Hz, H-1aα), 5.441 (m, 1H, H-8c)

IR; $\nu_{max}^{NaCl}$ cm$^{-1}$, 3400, 1745, 1375, 1230

Compound (17)

500 MHz $^1$H-NMR (CDCl$_3$, TMS) δH; 1.129(s, 4.5H, $^t$Bu), 1.139 (s, 4.5H, $^t$Bu), 1.867-2.211 (18s, 33H, Ac), 1.674 (t, 1H, J=12.5Hz, H-3cax), 2.563 (dd, 0.5H, J=4.8, 13.2Hz, H-3ceq), 2.570 (dd, 0.5H, J=3.7, 12.1Hz, H-3ceq), 3.008 (m, 1H, H-9c), 3.833 (s, 1.5H, OCH$_3$), 3.837 (s, 1 5H, OCH$_3$), 3.906 (m, 1H, H-9c), 4.090 (q, 0.5H, J=10.6Hz, H-5c), 4.095 (q, 0.5H, J=10.6Hz, H-5c), 4.576 (d, 0.5H, J=8.1Hz, H-1b), 4.580 (d, 0.5H, J=8.1 Hz, H-1b), 4.979 (dd, 0.5H, J=3.7Hz, 10.3Hz, H-2a α), 5.072 (dd, 0.5H, J=8.5, 9.9Hz, H-2a β), 5.209 (dd, 1H, J=3.3, 9.5Hz, H-7c), 5.258 (m, 1H, H-8c), 5.490 (t, 0.5H, J=9.5Hz, H-3a α),5.722 (d, 0.5H, J=8.4Hz, H-1a β), 6.261(dd, 1H, J=5.9, 11.0Hz, NH-9c), 6.309 (d, 0.5H, J=4.0Hz, H-1a α)

Elementary analysis C$_{49}$H$_{70}$N$_2$O$_{29}$ 1/6 CHCl$_3$

Calculation C 50.43 H 6.05 N 2.39

Found C 50.56 H 6.02 N 2.40

Reference Example 3

Compound (17)→(18)

125 mg (0.109 mmol) of compound(17) was dissolved in 2 ml of N,N-dimethylformamide. 14.3 mg (0.156 mmol) of hydrazine acetate was added to the solution and stirred at 60° C. for 15 minutes. The reaction solution was diluted with chloroform and washed with a saturated sodium hydrogen carbonate solution and saturated saline solution. The organic solution was dried over anhydrous magnesium sulfate and evaporated to dryness. The residue was purified over silica gel column chromatography (C-300, 20 g, carbon tetrachloride:acetone=1:2) to obtain 120.4 mg of compound(18) (yield: 100%).

Rf=0.176 (carbon tetrachloride:acetone=1:2)

$[\alpha]^{22}_D$ 34.6° (C=1.1, CHCl$_3$)

500 MHz $^1$H-NMR (CDCl$_3$, TMS) δH; 1.184(s, 9H, $^t$Bu), 1.867, 1.986, 1.999, 2 013, 2.061, 2.093, 2.118, 2.128, 2.160, 2.178, 2.195(11S, 33H, Ac), 2.568 (dd, 1H, J=4.8, 12.5Hz, H-3ceq), 2.909 (d, 0.6H, J=3.7Hz, OH-1a α), 3.038 (td, J=5.5, 15.4Hz, H-9c), 3.573 (dd, 1H, J=2.6, 10.6Hz, H-6c), 3.621 (d, 0.4H, J=8.8Hz, OH-1a β), 3.834 (s, 3H, OCH$_3$), 4.093(q, 1H, J=10.6Hz, H-5c), 4.524 (dd, 1H, J=3.7, 10.3Hz, H-3b), 4.589 (d, 1H, J=7.7Hz, H-1b), 4.695 (t, 0.4H, J=9.8Hz, H-1a β), 4.768 (t, 0.4H, J=10.3Hz, H-2a β), 4.783(dd, 0.6H, J=3.7, 10.3Hz, H-2a α), 4.869 (ddd, 1H, J=4.8, 10.3 , 11.7Hz, H-4c), 4.897 (d, 1H, J=2.2Hz, H-4b), 4.932 (dd, 1H, J=8.1, 8.9Hz, H-2b), 5.074 (d, 1H, J=9.9Hz, NH), 5.207(dd, 1H, J=2.9, 9.9Hz, H-7c), 5.403 (t, 1H, J=3.7Hz, H-1a α), 5.552(t, 0.6H, J=9.9Hz, H-3a α), 6.275 (t, 0.4H, J=5.9Hz, NH-9c β), 6.304 (t,0.6H, J=5.9Hz, NH-9c α)

Elementary analysis C$_{47}$H$_{68}$N$_2$O$_{28}$ 1/6 CHCl$_3$

Calculation C 50.18 H 6.09 N 2.48

Found C 50.33 H 6.20 N 2.33

Example 4

Compound (18)→(1)

109.5 mg (0.0 mmol) of compound (18) was dissolved in 1 ml of 1,2-dichloroethane. 358 μl (3.57 mmol) of trichlroacetonitrile and 358 μl (2.54 mmol) of 1,8-diazabicyclo[5.4.0]-7-undecene were added to the solution at 0° C. and stirred for 30 minutes. The reaction mixture was purified over silica gel column chromatography (C-300, 20 g, carbon tetrachloride acetone=1:1, C-300, 50 g, carbon tetrachloride acetone=1:1) to obtain 52 mg of compound (1) (yield: 43%).

Rf=0.50 (carbon tetrachloride acetone=1:2)

500 MHz $^1$H-NMR (CDCl$_3$, TMS) δH; 1.124(s, 9H, $^t$Bu), 1.865, 1.983, 2.005, 2.011, 2.064, 2.091, 2.120, 2.137, 2.208 (9s, 30H, Ac), 2.571 (dd, 1H, J=4.8, 12.5Hz, H-3ceq), 2.978(td, 1H, J=5.5, 14.7Hz, H-9c), 3.568 (dd, 1H, J=2.6, 11.0Hz, H-6c), 3.837 (s, 3H, OCH$_3$), 3.948 (t, 1H, J=9.9Hz, H-4a), 4.095 (q, 1H, J=10.6Hz, H-5c), 4.543 (dd, 1H, J=3.3, 9.9Hz, H-3b), 4.624 (d, 1H, J=8.1Hz, H-1b), 4.869 (dt, 1H, J=4.8, 11.7Hz, H-4c), 4.902 (d, 1H, J=2.9Hz, H-4b), 4.948 (dd, 1H, J=8.1, 9.9Hz, H-2b), 5.053 (d, 1H, J=11.0Hz, NH-5c),5.071 (dd, 1H, J=3.7, 10.3Hz, H-2a), 5.202 (dd, 1H, J=2.6, 9.5Hz, H-7c), 5.251 (m, 1H, H-8c), 5.594 (t, 1H, J=9.9Hz, H-3a), 6.244 (t, 1H, J=5.9Hz, NH-9c ), 6.522 (d, 1H, J=3.7Hz, H-1a α), 8.644 (s, 1H, c=NH)

Example 5

Compound (1)→(2)

64.1 mg (85 μmol) of benzoyl ceramide, 52 mg (40.7 μmol) of compound (1) and 1.1 ml of chloroform were added to Molecular Sieve 4 A under argon atmosphere and stirred at 20° C. for 15 minutes. Then 9.0 μl (73.5 μmol) of BF$_3$·Et$_2$O was added to the mixture at 0° C. and stirred for 18 hours under the same conditions. The reaction solution was filtered with Celite and distilled under reduced pressure. The residue was purified by silica gel column chromatography (C-300, 25 g, chloroform:methanol=20:1) to obtain 9.5 mg of compound (2) (yield: 12.6%).

Rf=0.611 (chloroform:methanol=10:1)

500 MHz $^1$H-NMR (CDCl$_3$, TMS) δH; 0.878(t, 3H, J=7.0Hz, CH$_3$), 0.880 (t, 3H, J=7.3Hz, CH$_3$), 1.149 (s, 9H, $^t$Bu), 1.254 (bs, 62H, —CH$_2$—), 1.864, 1.961, 1.983, 2.003, 2.008, 2.070, 2.080, 2.110, 2.120, 2.149 (10s, 30H, Ac), 2.555 (dd, 1H, J=4.8,12.8Hz, H-3ceq), 3.106(dt, 1H, 5 1, 14.7Hz, H-9c), 3.830 (s, 3H, OCH$_3$), 4.426 (d, 1H, J=8.1Hz, H-1a),4.469(m, 1H, H-2cer), 4.534 (d, 1H, J=8.1Hz, H-1b), 4.543 (dd, 1H, J=3.3, 10.3Hz, H-3b), 4.927(dd, 1H, J=7.7, 9.9Hz, H-2a), 5.190 (t, 1H, J=9.5Hz, H-3a), 5.216 (dd, 1H, J=2.6, 9.5Hz, H-7c), 5.249 (m, 1H, H-8c), 5.456 (dd, 1H, J=7.7, 15.4Hz, H-4'cer), 5.538 (t, 1H, J=7.7Hz, H-3cer), 5.731 (d, 1H, J=9.2Hz, NHcer),5.869(dt, 1H, J=6.6, 15.4Hz, H-5'cer), 6.340 (t, 1H, J=6.2Hz, NH-9c), 7.421 (t, 2H, J=8.1Hz, Ph(m)), 7.545 (t, 1H, J=7.3Hz, Ph(p)), 7.987 (dd, 2H, J=1.5, 8.4Hz, Ph(o))

Example 6

Compound (2)→(3)

4.1 mg (2.2 μmol) of compound (2) was dissolved in a mixture of 1 ml of methanol and 1 ml of tetrahydrofuran. 20 μl of sodium methoxide was added to the mixture and stirred at 20° C. for 18 hours. The reaction solution was distilled under reduced pressure. The residue was dissolved in a mixture of 1 ml of methanol, 1 ml of tetrahydrofuran and 1 ml of water, and stirred at 20° C. for 18 hours followed by distillation under reduced pressure. The residue was purified by Sephadex LH-20 (chloroform:methanol=1:1) to obtain 2.9 mg of compound (3) (yield: 100%).

Rf=0.656 (n-butanol:ethanol:water=2:2:1)

500 MHz $^1$H-NMR (CDCl$_3$:CD$_3$OD=1:1, TMS) δH, 0.891 (t, 6H, J=7.0Hz, CH$_3$), 1.245 (6s, 62H, —CH$_2$—), 1.590 (m, 2H, H-6cer), 1.781 (t, 1H, J=13.0Hz, H-3cax), 2.001 (s, 3H, Ac), 2.033(s, 3H, Ac), 2.178 (t, 2H, J=7.7Hz, NHCOCH$_2$—CH$_2$—), 2.819 (bd,1H, J=13.2Hz, H-3ceq),4.093 (t, 1H, J=8.1Hz, H-3cer), 4.220 (dd, 1H, J=4.0, 9.9Hz, H-3b), 4.301(d, 1H, J=7.7Hz, H-1a), 4.414(d, 1H, J=7.7Hz, H-1b), 5.457(dd, 1H, J=7.7, 15.4Hz, H-4' cer), 5.693 (td, 1H, J=6.6, 15.4Hz, H-5'cer)

Example 7

Compound (C)+(E)→(21)

100 mg (198 μmol) of compound (C) dissolved in 1.5 ml of acetonitrile and 348 mg (396 μmol) of compound (E) dissolved in 1.5 ml of acetonitrile were added to 300 mg of MS-3A and 300 mg of MS-4A under argon atmosphere, and stirred for 30 minutes. Then 76.5 mg (298 μmol) of AgOTf dissolved in 1 ml of acetonitrile and 57.0 mg (297 μmol) of PhSeCl were added to the solution respectively under cooling at −15° C. and stirred at 20° C. for 18 hours. The reaction solution was diluted with chloroform and filered through Celite and the resulting organic layer was washed with an aqueous sodium hydrogen carbonate solutoin and saturated saline solution, and dried over anhydrous magnesium sulfate. The resulting solution was evaporated to dryness. The residue was purified by silica gel column chromatography (C-300, 50 g, toluene:ethyl acetate=1:1 and then 1:2) to obtain 108.8 mg of compound (21) (yield: 41.3%).

Rf=0.29

$[\alpha]^{26}_D$ −12.7° (C=0.4, CHCl$_3$)

500 MHz $^1$H-NMR (CDCl$_3$, TMS) δH,1.126(s, 9H, $^t$Bu), 1.774 (t, 1H, J=12.1Hz, H-3cax), 1.890, 2.047, 2.124, 2.148 (4s, 12H, Ac), 3.771 (s, 3H, OCH$_3$), 4.073 (t, 1H, J=9.2Hz, H-4a), 4.089 (q, 1H, J=10.3Hz, H-5c), 4.428 (d, 1H, J=12.8Hz, CH$_2$Ph), 4.449 (d, 1H, J=8.1Hz, H-1a), 4.473 (d, 1H, J=8.1Hz, H-1b), 4.556, 4.594 (2d, 2H, J=12.1Hz, CH$_2$Ph), 4.603 (d,1H, J=11.0Hz, CH$_2$Ph), 4.653 (d, 1H, J=11.7Hz, CH$_2$Ph), 4.746 (d, 1H, J=11.0, CH$_2$Ph), 4.777 (d, 1H, J=11.7Hz, CH$_2$Ph), 4.785 (d, 1H, J=11.0Hz, CH$_2$Ph), 4.836 (ddd, 1H, J=4.8, 9.9, 12.1Hz, H-4c), 4.868 (d, 1H, J=12.1Hz, CH$_2$Ph), 4.944(d, 1H, J=11.0Hz, CH$_2$Ph), 5.121 (dd, 1H, J=7.7, 9.5Hz, H-2a), 5.133 (d, 1H, J=10.3Hz, NH), 5.219(dt, 1H, J=3.3, 6.6Hz, H-8c), 5.326 (dd, 1H, J=1.8, 6.6Hz, H-7c)

Elementary analysis C$_{70}$H$_{84}$N$_4$O$_{22}$ ⅓ CHCl$_3$
Calculation C 61.52 H 6.19 N 4.08
Found C 61.42 H 6.27 N 4.39

Synthesis of compound (E)

O-(2,3-di-O-benzyl-4,6-O-benzyliden-β-D-galactopyranosyl)-(1→4)-3,6-di-O-benzyl-2-O-pivaloyl-β-D-glucopyranoside (4.00 g, 4.144 mmol) which is a known compound was dissolved in 50 ml of CH$_2$Cl$_2$. 4 ml of 90% CF$_3$COOH aqueous solution was added to the solution and stirred at room temperature for 15 minutes. The reaction mixture was diluted with CHCl$_3$ (50 ml) and washed with a saturated NaHCO$_3$ solution (30 ml) and a saturated NaCl solution (30 ml). The solution was dried with MgSO$_4$ and the solvent was distilled under reduced pressure. The residue was purified by flash chromatography (C-300, 200 g, 1:4 AcOEt-toluene) to obtain compound (E) (3.02 g, 83%).

Physical chemical properties of compound (E)

$[\alpha 9^{27}_D$ −2.9° (C=0.97 in CHCl$_3$)

mp 131° to 134° C. (recrystalized from CCl$_4$)

TLC: Rf 0.32 (3:1 toluene - THF)

$^1$H-NMR (500 MHz CDCl$_3$, TMS, 24°):

δ$_H$ 5.118 (dd, 1H, J=7.9, 9.3 Hz, H-2a),
4.478 (d , 1H, J=8.1 Hz, H-1a),
4.374 (d , 1H, J=8.1 Hz, H-1b),
4.030 (t , 1H, J=9.3 Hz, H-4a),
3.866 (d , 1H, J=2.9 Hz, H-4b),
3.628 (t , 1H, J=9.2 Hz, H-3a),
3.602 (dd, 1H, J=7.9 9.3 Hz, H-2b),

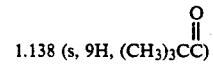

1.138 (s, 9H, (CH$_3$)$_3$CC)

Reference Example 4

Compound (21)→(22)

274 mg (0.21 mmol) of compound (21) was dissolved in a mixture of 3 ml of pyridine and 3 ml of acetic anhydride. 51 mg of 4-dimethylaminopyridine was added to the mixture and stirred at 20° C. for 18 hours. The reaction mixture was distilled under reduced pressure and the residue was purified by silica gel column chromatography (C-300, 50 g, toluene:methanol=12:1) and Sepahdex LH-20 (elution with methanol) to obtain 277 mg of compound (22) (yield: 98%).

Rf=0.39 (toluene:metahnol=7:1)

$[\alpha]^{28}_D$ −10.2° (C=0.5, CHCl$_3$)

500 MHz $^1$H-NMR (CDCl$_3$, TMS) δH; 1.124(s, 9H, $^t$Bu), 1.880, 2.022, 2.094, 2.102, 2.119(5s, 15H, Ac), 2.472 (dd, 1H, J=4.9, 12.8Hz, H-3ceq), 3.164 (dd, J=5.9Hz, 13.6Hz, H-9c), 3.753 (s, 3H, OCH$_3$), 4.060 (q, 1H, J=10.3Hz, H-5c), 4.130 (t, 1H, J=9.2Hz, H-4a), 4.443(d, 1H, J=12.5Hz, CH$_2$Ph), 4.453 (d, 1H, J=11.0Hz, CH$_2$Ph), 4.479 (d, 1H, J=8.1Hz, H-1a), 4.560 (d, 1H, J=7.7Hz, H-1b), 4.571, 4.597 (2d,2H, J=12.8Hz, CH$_2$Ph), 4.655, 4.694, 4 757 (3d, 3H, J=11.0Hz, CH$_2$Ph), 4.765 (d, 1H, J=11.4Hz, CH$_2$Ph), 4.822 (ddd, 1H, J=4.5, 9.3, 11.6Hz, H-4c), 4.872 (d, 1H, J=12.1Hz, CH$_2$Ph), 4.889 (d, 1H, J=11.0Hz, CH$_2$Ph), 5.160 (d, 1H, J=9.5Hz, NH), 5.149 (dd, 1H, J=8.1, 9.2Hz, H-2a), 5.191 (m, 1H, H-8c), 5.300 (dd, 1H, J=1.8, 7.3Hz, H-7c), 5.472 (d, 1H, J=2.9Hz, H-4b)

Reference Example 5

Compound(22)→(23)

268 mg (0.20 mmol) of compound (22) was dissolved in 10 ml of methanol. 464 mg (4.54mmol) of acetic anhydride and 200 mg of 20% palladium hydroxide were added to the solution and catalytic reduction was conducted at 0° C. for 18 hours. The reaction solution was filtered by a chromatodisc (25 N, 0.45 μm) and evaporated to dryness to obtain 180 mg of compound (23) (yield: 100%)

Rf=0.58 (ethyl acetate:ethanol:water=5:2:1)

500 MHz $^1$H-NMR (CD$_3$OD, TMS) δH; 1.258, 1.264 (2s, 9H, $^t$Bu), 1.823-2.203 (18H, Ac), 2.545 (dd, 1H, J=5.0, 12.6Hz, H-4c), 3.803(s, 3H, OCH$_3$), 4.419 (d, 1H,

J=7.7Hz, H-1b), 4.592 (dd, 0.5H, J=3.7, 9.9Hz, H-2aα), 4.678 (t, 0.5H, J=7.7Hz, H-2aβ), 5.146(dd, 1H, J=1.5, 8.8Hz, H-7c), 5.212 (d, 0.5H, J=3.7Hz, H-1a α), 5.259 (d, 1H, J=3.7Hz, H-4b), 5.273 (m, 1H, H-8c)

Reference Example 6

Compound (23)→(24)

180 mg (0.195 mmol) of compound (23) was dissolved in a mixture of 2 ml of pyridine and 2 ml of acetic anhydride. 51 mg of 4-dimethylaminopyridien was added to the mixture and stirred at 20° C. for 18 hours. The reaction solution was distilled and the residue was purified by silica gel column chromatography (C-300, 25 g, toluene:methanol=9:1) and Sepahdex LH-20 (methanol) to obtain 169 mg of compound (24) (yield: 76.8%).

Rf=0.14 (toluene:methanol=9:1)

500 MHz $^1$H-NMR (CDCl$_3$, TMS) δH 1.128(s, 4.5H, $^t$Bu), 1.138 (s, 4.5H, $^t$Bu), 1.904-2.222 (33H, Ac), 2.542 (dd, 1H, J=4.4, 12.8 Hz, H-3ceq), 2.942 (m, 1H, H-9c), 3.818 (s, 1.5H, OCH$_3$), 3.834 (s, 1.5H, OCH$_3$), 4.615(d, 0.5H, J=7.0Hz, H-1b), 4.637 (d, 0.5H, J=8.1 Hz, H-1b), 4.801 (m, 1H, H-4c), 5.146 (d,1H, J=9.9Hz, NH), 5.323(t, 0.5H, J=9.2Hz, H-3aα or α), 5.493 (t, 0.5H, J=9.9Hz, H-3aα or β), 5.731 (d, 0.5H, J=8.4Hz, H-1a β), 6.171 (dd, 1H, J=7.0, 12.1Hz, NH-9c), 6.295 (d, 0.5H, J=4.0Hz, H-1a α)

Elementary analysis C$_{49}$H$_{70}$N$_2$O$_{29}$ 1/6 CHCl$_3$
Calculation C 50.43 H 6.05 N 2.39
Found C 50.21 H 6.00 N 2.41

Reference Example 7

Compound (24)→(25)

154.5 mg (0.13 mmol) Of compound (24) was dissolved in 2 ml of dimethylformamide. 15.2 mg (0.16 mmol) of hydrazine acetate was added to the solution at 60° C. and stirred for 5 minutes. Then the reaction mixture was diluted with chloroform and the organic layer was washed with an aqueous sodium hydrogen carbonate solution and saturated saline solution followed by drying with anhydrous magnesium sulfate. The resulting solution was distilled and the residue was purified by silica gel column chromatography (C-300, 24 g, chloroform:methanol=20:1) to obtain 124 mg of compound (25) (yield: 83%).

Rf=0.19 (chloroform:methanol=20:1)

500 MHz $^1$H-NMR (CDCl$_3$, TMS) δH; 1.184(s, 2.7H, $^t$Bu), 1.190 (s, 6.3H, $^t$Bu), 1.893-2.233 (30H, Ac), 2.526(dd, 0.7H, J=4.8, 13.2H, H-3ceq), 2.553 (dd, 0.3H, J=4.8, 13.2Hz, H-3ceq), 3.788 (s, 2.1H, OCH$_3$), 3.808 (s, 0.9H, OCH$_3$), 4.101 (q, 1H, J=10.3Hz, H-5c), 4.617 (d, 0.3H, J=7.7Hz, OH-1aβ), 4.733 (t, 0.3H, J=8.4Hz, H-1a β), 4.975 (dd, 0.7H, J=3.7, 10.6Hz, H-3b α), 4.981 (dd, 0.3H, J=2.7, 10.6Hz, H-3b β), 5.109 (dd, 1H, J=2.6, 10.3Hz, H-7c), 5.175 (m, 1H, H-8c), 5.357 (t, 0.3H, J=9.2Hz, H-3aβ), 5.379 (t, 0.7Hz, J=3.7Hz, H-1aα), 5.436 (d, 1H, J=3.3Hz, H-4b), 5.768 (t, 0.7H, J=9.9Hz, H-3aα)

Elementary analysis C$_{47}$H$_{68}$N$_2$O$_{28}$ ⅓ CHCl$_3$
Calculation C 49.49 H 6.00 N 2.53
Found C 49.78 H 5.98 N 2.52

Example 8

Compound (25)→(4)

120 mg (0.11 mmol) of compound (25) was dissolved in 1 ml of 1,2-dichloroethane. 179 μl (1.79 mmol) of trichloroacetonitrile and 12 μl (0.085 mmol) of DBU were added to the solution and stirred at 0° C. for 1 hour. The reaction solution was purified by silica gel column chromatography (C-300, 20 g, chloroform:acetone=1:1) to obtain 118 mg of compound (4) (yield: 88%)

Rf=0.58 (chloroform:acetone=1:2)
[α]$_D^{22}$ 26.5° (C=0.4, CHCl$_3$)
500 MHz $^1$H-NMR (CDCl$_3$, TMS) δH; 1.136(s, 9H, $^t$Bu), 1.905, 1.946, 1.974, 2.035, 2.047, 2.099, 2.112, 2.151, 2.211, 2.356 (10s, 30H, Ac), 5.238 (dd, 1H, J=4.8, 13.2Hz, H-3ceq), 2.949 (m, 1H, H-9c), 3.811 (s, 3H, OCH$_3$), 3.929 (t, 1H, J=9.9Hz, H-4a), 4.103 (q, 1H, J10.3Hz, H-5c), 4.478 dd, 1H, J=1.5, 11.7 Hz, H-6c), 4.661 (d, 1H, J=8.1Hz, H-1b), 4.797 (ddd, 1H, J=4.4, 10.3, 12.5Hz, H-4c), 4.991 (dd, 1H, J=3.3, 10.3Hz, H-3b), 5.469 (d, 1H, J=3.3Hz, H-4b), 5.590 (t, 1H, J=9.5Hz, H-3a), 6.170 (dd, 1H, J=4.8, 7.7Hz, NH-9c), 6.515 (d, 1H, J=3.7Hz, H-1a α), 8.643 (s, 1H, =NH)

Example 9

Compound (4)→(5)

144.5 mg (0.19 mmol) of benzoyl ceramide dissolved in 1 ml of chloroform and 117 m9 (0.092 mmol) of compound (4) dissolved in 1 ml of chloroform were added to 600 mg of activated Molecular Sieve 4A under argon atmosphere and stirre for 5 minutes. 20.2 μl (0.17 mmol) of BF$_3$·Et$_2$O was added to the resulting mixture, and stirred for 3 hours at 0° C., and for 18 hours at room temperature. The reaction mixture was diluted with chloroform and filtered with Celite followed by evaporation to dryness. The residue was purified by silica gel column chromatography (C-300, 20 g, chloroform:acetone=3:2 and chloroform:acetone=2:3) to obtain 90.1 mg of compound (5) (yield: 53.3%).

Rf=0.48 (chloroform:methanol=15:1)
[α]$_D^{26}$ −2.2° (C=0.2, CHCl$_3$)
500 MHz $^1$H-NMR (CDCl$_3$, TMS) δH; 0.878(t, 3H, J=7.0Hz, CH$_3$), 0.880 (t, 3H, J=7.7Hz, CH$_3$), 1.144 (s, 9H, $^t$Bu), 1.255 (bs, 62H, —CH$_2$—), 1.907, 1.935, 1.950, 1.967, 2.015, 2.021, 2.036, 2.094, 2.138, 2.223 (10s, 30H, Ac), 2.544 (dd, 1H, J=4.8, 12.8Hz, H-3ceq), 2.918(m, 1H, H-9c), 3.815 (s, 3H, OCH$_3$), 4.107(q, 1H, J=10.3Hz, H-5c), 4.324 (dd, 1H, J=1.8, 12.1Hz, H-6c), 4.441 (d, 1H, J=7.7Hz, H-1a),4.580 (d, 1H, J=7.7Hz, H-1b), 4.803 (ddd, 1H, J=4.8, 10.6, 12.1Hz, H-4c), 4.912 (dd, 1H, J=7.7, 9.2Hz, H-2a), 4.970 (dd, 1H, J=3.3, 10.6Hz, H-3b), 5.141 (d, 1H, J=10.3Hz, NH-5c), 5.226 (t, 1H, J=9.5Hz, H-3a), 5.440 (d, 1H, J=2.2Hz, H-4b), 5.462 (dd, 1H, J=7.7, 15.4 Hz, H-4'cer), 5.548 (t, 1H, J=7.3Hz, H-3cer), 5.827 (d, 1H, J=9.2Hz, NHcer), 5.863 (td, 1H, J=7.0, 15.0Hz, H-5'cer), 6.172 (dd, 1H, J=4.4, 7.7Hz, NH-9c)

Elementary analysis C$_{96}$H$_{153}$N$_3$O$_{31}$ ⅓ CHCl$_3$
Calculation C 61.38 H 8.20 N 2.23
Found C 61.41 H 8.19 N 2.31

Example 10

Compound (5)→(6)

79.7 mg (43.1 μmol) of compound (5) was dissolved in a mixture of 4 ml of methanol and 2 ml of tetrahydrofuran. 100 μl (0.1 mmol) of 1N- sodium methoxide was added to the mixture and stirred at 20° C. for 6 hours. The reaction solution was evaporated to dryness under reduced pressure. The residue was dissolved in a mixture of 2 ml of methanol, 2 ml of tetrahydrofuran and 0.5 ml of water, and stirred at 20° C. for 18 hours. The reaction solution was evaporated to dryness and the residue was purified by Sephadex LH-20 (eluted with methanol:chloroform=1:1) to obtain 56.3 mg of compound(6) (yield: 100%).

Rf=0.57 (butanol:ethanol:water=2:2:1)

[α]$_D^{26}$ −6.0 (C=0.2, CHCl$_3$:MeOH=1:1)

500 MHz $^1$H-NMR (CDCl$_3$:CD$_3$OD=1:1, TMS) δH 0.853 (t,6H, J=6.8Hz, CH$_3$), 1.237 (bs, 62H, —CH$_2$—), 1.553 (m, 2H, H-6cer), 1.707 (t, 1H, J=12.1Hz, H-3cax), 1.990 (s, 3H, NAc), 1.963(s, 3H, NAc), 2.145 (t, 2H, J=7.3Hz, NHCOC$\underline{H_2}$—CH$_2$), 2.729 (bd,1H, J=12.9Hz, H-3ceq),4.059 (t, 1H, J=8.1Hz, H-3cer), 4.161 (dd,1H, J=3.9, 9.4Hz, H-3b), 4.276 (d, 1H, J=7.7Hz, H-1a), 4.284 (d, 1H, J=7.7Hz, H-1b), 5.423 (dd, 1H, J=7.7, 15.1Hz, H-4'cer), 5.668 (dt, 1H, J=6 1, 15.5Hz, H-5'cer)

Reference Example 8

Compound (G)→(H)

1.30 g (2.81 mmol) of compound (G) was dissolved in 50 ml of pyridine. 417 mg (3.65 mmol) of methanesulfonyl chloride was added to the solution and stirred at 20° C. for 6 hours. The reaction solution was evaporated and the residue was purified by silica gel column chromatography (C-300, 100 g, chloroform:methanol=20:1) to obtain 1.5 g of compound (H) (yield: 98.7%).

Rf=0.586 (ethyl acetate:methanol=50:1)

[α]$_D$ −8.7° (C=0.4, chloroform)

500 MHz $^1$H-NMR (CDCl$_3$, TMS) δ$_H$; 1.613(s, 3H, Ac), 1.885(s, 3H, Ac), 2.035(s, 6H, Ac),2.635(dd, 1H, J=4.4, 12.8Hz, H-3eq), 3.030 (s, 3H, OSO$_2$CH$_3$), 3.800 (s, 3H, OCH$_3$), 3.895 (tdd, 1H, J=1.5, 5.9, 12.5Hz, —OC$\underline{H_2}$CH—),4.193(dd, 1H, J=5.5, 11.7Hz, H-9'), 4.274(tdd, 1H, J=1.5, 5.1, 12.8Hz, —OC$\underline{H_2}$CH—), 4.525(dd, 1H, J=2.6, 11.4Hz, H-9), 4.868(ddd, J=1.5, 2.9, 10.3 Hz,

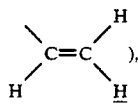

5.216(d, 1H, J=9.2Hz, NH), 5.295(ddd, 1H, J=1.5, 3.3, 17.2Hz,

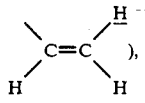

5.350(dd, 1H, J=1.8, 1H, J=4.8, 9.9, 12.1Hz, H-4), 5.177(ddd, 1H, 7.7Hz, H-7), 5.411(ddd, 1H, J=2.6, 5.5, 7.7 Hz, H-8), 5.859(tdd, 1H, J=5.1, 10.3, 17.2Hz, CH$_2$—C$\underline{H}$=CH$_2$)

Reference Example 9

Compound (H)→(J)→(K)→(L)

200 mg (0.369 mmol) of compound (H) was dissolved in 30 ml of dimethylformamide. 36 mg (0.554 mmol) of sodium azide was added to the solutoin and stirre at 100° C. for 20 hours. The reaction solution wa evaporated under reduced pressure. (compound (J); Rf=0.667, butanol:ethanol:water=2:1:1)

The residue was dissolved in a mixture of 4 ml of pyridine and 4 ml of acetic anhydride. A catalytic amount of 4-dimethylaminopyridine was added to the mixture and stirred at 20° C. for 68 hours. The reaction solution was evaporated under reduced pressure and the residue was dissolved in ethyl acetate. The resulting organic layer was washed with waster and acidified with diluted hydrochloric acid solution. The aqueous acid solution was subjected to re-extraction with chloroform and the combined organic layer was dried over anhydrous magnesium sulfate followed by distillation under reduced pressure. (compound (K))

The residue was dissolved in 1 ml of methanol and diazomethane-ether solution was added thereto and allowed to stand for 30 minutes. Then the solution was distilled under reduced pressure and the residue was purified by silica gel column chromatography (C-300, 25 g, ethyl acetate:methanol=100:1) to obtain 141 mg of compound (L) (yield: 78%).

Rf=0.489 (ethyl acetate:methanol=100:1)

[α]$^{23}_D$ −6.0° (C=1.2, CHCl$_3$)

500 MHz $^1$H-NMR (CDCl$_3$, TMS) δ$_H$; 1.885 (s, 3H, Ac), 1.988(t, 1H, J=12.5Hz, H-3ax), 2.032, 2.164, 2.179(3s, 9H, Ac), 2.625(dd, 1H, J=4.8, 12.8Hz, H-3eq), 3.294(dd, 1H, J=5.9, 12.5Hz, H-9'), 3.591(dd, 1H, J=2.6, 1H, J=6.3, 12.5Hz, —OC$\underline{H_2}$—CH=), 4.262dd, 1H, J=5.5, 12.5Hz, —OC$\underline{H_2}$—CH=), 4.853(m, 1H, H-4), 5.175(dd, 1H, J=1.5, 10.6Hz,

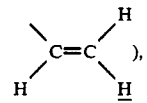

5.215(d, 1H,J=9.2Hz, NH), 5.293(dd, 1H, J=1.5, 17.2Hz,

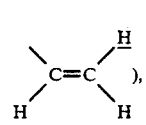

5.861(tdd, 1H, 12.1Hz, H-9), 3.800(s, 3H, OCH$_3$), 3.891(dd, J=5.5, 10.3,17.2 Hz, CH$_2$—C$\underline{H}$=CH$_2$)

IR, ν$_{max}^{NaCl}$, cm$^{-1}$, 2110, 1748, 1230, 1210

Reference Example 10

Compound (L)→(M)

71 mg (0.145 mmol) of compound (L) was dissolved in 2 ml of benzene. 87 mg (0.331 mmol) of triphenylphosphine and 20 μl of water were added to the solution and refluxed for 20 hours. The reaction solution was distilled and the residue was purified by Sephadex LH-20 (elution with methanol). The residue was dissolved in a mixture of 1 ml of pyridine and 1 ml of acetic anhydride. A catalytic amount of 4-dimethylaminopyridine was added to the mixture and stirred at 20° C. for 92 hours. The reaction solution was distilled under reduced pressure and the residue was purified by silica gel column chromatography (C-300, 10 g, chloroform:acetone=2:1 and chloroform:methanol=10:1) to obtain 55 mg of compound (M) (yield: 75.3%).

Rf=0.806 (chloroform:acetone=1:1)

[α]$_D^{22}$ 12.9° (C=0.9, CHCl$_3$)

500 MHz $^1$H-NMR (CDCl$_3$, TMS) δ$_H$; 1.907, 1.987, 2.044, 2.124, 2.207(5s, 15H, Ac), 2.620(dd, 1H, J=4.8, 12.8Hz, H-3eq), 2.808 (td, 1H, J=4.4, 14.2Hz, H-9), 3.772(s, 3H, OCH$_3$), 3.869(tdd, 1H, J=1.5, 5.9, 12.8Hz, —OC$\underline{H_2}$—CH=), 4.048(dd, 1H, J=2.2, 10.6Hz, H-6), 4.074(ddd, 1H, J=3.3, 8.4, 13.6Hz, H-9), 4.282(tdd, 1H, J=1.5, 5.1, 12.8Hz, —OCH₂—CH=), 4.835 (ddd, 1H, J=4.8, 10.3, 12.1Hz, H-4), 5.100(dd,1H, J=2.2, 9.5Hz, H-7), 5.193(td, 1H, J=3.3, 9.5Hz, H-8), 5.234(d, 1H, NH), 5.286(ddd, 1H, J=1.5, 3.3, 17.2Hz,

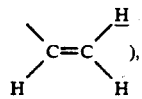

5.855(tdd, 1H, J=5.1, 11.0, 17.2Hz, —CH₂=CH₂), 6.132(dd, 1H, J=4.8, 7.7Hz, 9-NH).

Reference Example 11

Compound (M)→(N)

Method I:
548 mg (10.9 mmol) of compound (M) was dissolved in 20 ml of a mixture (ethanol:water:acetic acid=20:5:1). 405 mg of 10% Pd-C was added to the mixture and stirred at 60° C. for 20 hours. The reaction solution was filtered through Chromatodisc 25N ® and distilled under reduced pressure. The residue was dissolved in 10 ml of 80% tetrahydrofuran aqueous solution and 600 mg of iodine was added to the reaction. And the reaction mixture was stirred for 30 minutes at 20° C. The reaction mixture was diluted with water and chloroform, and the organic layer was washed with an aqueous sodium hydrogen sulfite solution and saturated saline solution. The resulting organic solution was dried over anhydrous magnesium sulfate and distilled under reduced pressure. The residue was purified by silica gel column chromatography (C-300, 100 g, chloroform:methanol=20:1) to obtian 410.8 mg of compound (N) (yield: 81.4%).

Rf=0.292 (chloroform:methanol=10:1)
$[\alpha]_D^{23}$ 15.3° (C=1.0, CHCl₃)
500 MH ¹H-NMR (CDCl₃, TMS) $\delta_H$; 1.910, 1.940, 2.008, 2.088, 2.170(5s, 15H, Ac), 3.093(m, 1H, H-9), 3.843(s, 3H, OCH₃), 4.085(ddd, 1H, J=3.7, 7.3, 14.2Hz, H-9), 4.172(q, 1H, J=10.3Hz, H-5), 4.233(dd, 1H, J=1.8, 10.6Hz, H-6), 5.090(m, 1H, H-4), 5.305(dd, 1H, J=1.8, 4.4Hz, H-7), 6.013(t, 1H, J=6.7Hz, NH-9).

Method II:
1 ml of tetrahydrofuran and 2.1 mg (1.8 μmol) of [Ir(COD)(PMePh₂)₂]PF₆ were added to a two-neck flask under N₂ atomsphore. Then N₂ gas was substituted with H₂ gas and H₂ gas was again substituted with N₂ gas. 47.7 mg (94.5 μmol) of compound (M) dissolved in 1 ml of tetrahydrofuran was added to the flask and stirred at 20° C. for 1 hour. The reaction solution was distilled under reduced pressure and the residue was dissolved in 3 ml of a mixture (tetrahydrofuran:water=4:1). 48 mg (378 mmol) of iodine was added to the mixture and stirred at 20° C. for 18 hours. The reaction solution was diluted with chloroform and the organic layer was washed with an aqueous sodium hydrogen sulfite solution and saturated saline solution. The resulting solution was dried over anhydrous magnesium sulfate and distilled under reduced pressure. The residue was purified by silica gel column chromatography (C-300, 15 g, chloroform:methanol=18:1) to obtain 25.8 mg of compound (N) (yield 58.7%).

Example 11

Compound (N)→(7)

50 mg (0.11 mmol) of compound (N) was dissolved in 1.5 ml of a mixed solvent of 1,2-dichloroethane and toluene (1:2). 80 μl (0.66 mmol) of diethylaminosulur trifluoride (DAST) was added to the mixture, and stirred for 30 minutes at −40° C. and for 30 minutes at 0° C. The reaction solution was distilled under reduced pressure and the residue was purified by silica gel column chromatography (C-300, 8 g, chloroform:methanol=20:1) to obtain 45.4 mg of compound (7) (yield: 90.4%).

Rf=0.42, 0.47 (chloroform:methanol=15:1)

Example 12

Compound (N)→(8)

50 mg (0.11 mmol) of compound (N) was dissolved in a mixture of 5 ml of 1,2-dichloroethane and 30 ml of acetyl chloride, and hydrogen chloride gas was introduced into the mixture under cooling at −10° C. and then was stirred for 18 hours at 20° C. The reaction solution was evaporated to dryness under reduced pressure to give 52 mg of compound (8) (yield: 100%).

Rf=0.34 (chloroform:methanol=15:1)

Reference Example 12

Compounds (8)+(D)→(31) and (32)

53 mg (0.21 mmol) of mercury cyanide, 24 mg (0.07 mmol) of mercury bromide and 228 mg (1.22 mmol) of compound (D) dissolved in 0.5 ml of 1,2-dichloroethane were added to 200 mg of activated Molecular Sieve 4A and stirred for 39 minutes. 71 mg (0.15 mmol) Of compound (8) dissolved in 1 ml of 1,2-dichloroethane was added to the mixture gradually under cooling at −10° C., and stirred for 3 hours and at 20° C. for 18 hours. The reaction solution was filtered with Celite and distilled under reduced pressure. The residue was purified by silica gel column chromatography (C-300, 13 g, toluene:ethyl acetate=1:3 and chloroform:methanol=15:1) to obtain compounds (31) and (32).

compound (31): 5.4 mg (yield: 2.5%)
Rf=0.48 (chloroform:methanol=15:1)
500MHz; ¹H-NMR(CDCl₃, TMS) $\delta_H$; 1.127(s, 9H, ᵗBu), 1.888, 1.910, 1.965, 2.022, 2.047(5s, 15H, Ac), 2.504(dd, 1H, J=4.8, 13.2Hz, H-3c eq), 2.673(td, 1H, J=4.4, 15.0Hz, H-9c), 2.759 (d, 1H, J=3.3Hz, OH), 3.624(t, 1H, J=9.2Hz, H-3a), 3.906(ddd, 1H, J=3.3, 7.7, 15.0Hz, H-9'c), 3.947(dd, 1H, J=2.2, 10.6 Hz, H-6c), 4.066(t, 1H, J=9.5Hz, H-4a), 4.141(q, 1H, J=10.6Hz, H-5c), 4.249, 4.336, (2d, 2H, J=11, 7Hz, CH₂Ph), 4.444(d, 1H, J=7.7Hz, H-1a), 4.552(d, 1H, J=7.7, H-1b), 4.692, 4.765(2d, 2H, J=11.7Hz, CH₂Ph), 4.852(d, 1H, J=12.1Hz, CH₂Ph), 4.980(d, 1H, J=10.6Hz, CH₂Ph), 5.085 (dd, 1H, J2.2, 8.4Hz, H-7c), 5.119(dd, 1H, J=8.1, 9.5Hz, H-2a), 5.186(d, 1H, J=9.9Hz, NH), 5.840(dd, 1H, J=5.1, 8.1Hz, NH-9c).

compound (32): 8.3 mg (yield: 12.7%)
Rf=0.38 (chloroform:methanol=15:1)
500 MHz ¹H-NMR(CDCl₃, TMS) $\delta_H$; 1.949, 1.997, 2.070, 2.094, 2.163(5s, 15H, Ac), 3.298(dd, 1H, J=4.4, 5.8, 15.0Hz, H-9), 3.840(s, 3H, OCH₃), 3.902(ddd, 1H, J=5.1, 7.0, 15.0Hz, H-9'), 4.423(q, 1H, J=10.3Hz, H-5), 5.084(dd, 1H, J=4.4, 4.6Hz, H-8), 5.387(dd, 1H, J=2.2, 4.8Hz, H-7), 5.564(dd, 1H, J=2.9, 8.8Hz, H-4), 5.660(d, 1H, J=8.8Hz, NH), 5.995(d, 1H, J=2.9Hz, H-3), 6.587(t, 1H, J=5.7Hz, NH-9).

Reference Example 13

Compound (31)→(33)

5.7 mg (3.8 μmol) of compound (31) was dissolved in a mixture of 1 ml of pyridine and 1 ml of acetic anhydride, and a catalytic amount of 4-dimethylaminopyridine was added followed by agitation at 20° C. for 20 hours. The reaction solution was distilled under reduced pressure and the residue was purified by silica gel column chromatography (C-300, 10 g, chloroform:methanol=20:1) and by sephadex LH-20 (elution with methanol) to obtain 5.9 mg of compound (33) (yield: 100%).

Rf=0.483 (chloroform:methanol=15:1)

500 MHz $^1$H-NMR(CDCl$_3$, TMS) $\delta_H$; 1.129(s, 9H, $^t$Bu), 1.845, 1.871, 1.899, 2.001, 2.019, 2.044(s, 18H, Ac), 2.559(dd, 1H, J=4.8, 12.5Hz, H-3ceq), 2.735(td, 1H, J=4.8, 15.0Hz, H-9c), 3.452(dd, 1H, J=7.7, 9.5Hz, H-2b), 3.810(s, 3H, OCH$_3$), 4.076(t, 1H, J=8.8Hz, H-4a), 4.152, 4.315(d, 2H, J=11.7Hz, C$\underline{H_2}$Ph), 4.158(q, 1H, J=10.3Hz, H-5c), 4.420(d, 1H, J=8.1Hz, H-1a), 4.153, 4.678(d, 2H, J=12.5Hz, C$\underline{H_2}$Ph), 4.705(d, 1H, J=7.3Hz, H-1b), 4.837 (d, 1H, J=12.1Hz, C$\underline{H_2}$Ph), 5.039(d, 1H, J=2.9Hz, H-4b), 5.089(dd, 1H, J=2.6, 9.2Hz, H-7c), 5.108(dd, 1H, J=8.1, 9.5Hz, H-2a), 5.164(d, 1H, J=10.3Hz, NH-5c), 5.354(td, 1H, J=4.0, 8.1Hz, H-8c), 5.985(dd, 1H, J=5.1, 12.8Hz, NH-9c).

Reference Example 14

Compound (32)→(17)

5.9 mg (3.9 μmol) of compound (32) was dissolved in 1 ml of methanol. 5 mg of 20% palladium hydroxide was added to the solution and catalytic reduction was conducted at 20° C. for 18 hours. The reaction solution was filtered through Chromatodisc (25 N ®, 0.45 μm) and distilled under reduced pressure. The residue was dissolved in a mixture of 1 ml of pyridine and 1 ml of acetic anhydride and a catalytic amount of 4-dimethylaminopyridine was added followed by agitation at 20° C. for 20 hours. The reaction solution was distilled under reduced pressure and purified by silica gel column chromatography (C-300, 10 g, toluene:methanol=9:1) and by Sephadex (elution with methanol) to obtain 4.1 mg of compound (17) (yield: 93%).

What we claim is:

1. A compound represented by formula (I) below:

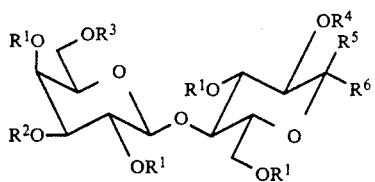

(I)

wherein $R^1$ represents hydrogen, and one of $R^2$ and $R^3$ represents a neuramic acid group represented by general formula (V):

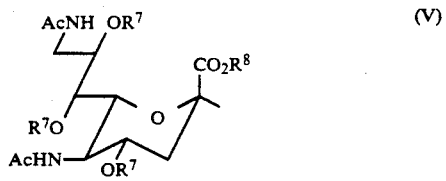

(V)

wherein $R^7$ represents hydrogen, $R^8$ represents a sodium atom and Ac means an acetyl group; the other of $R^2$ and $R^3$ represents hydrogen; $R^4$ represents hydrogen; $R^5$ represents

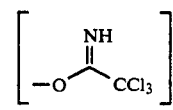

or hydrogen; $R^6$ represents a ceramide group represented by formula (VI):

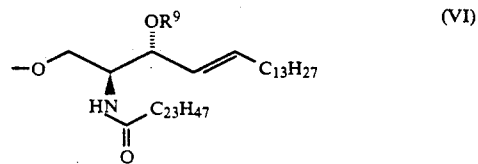

(VI)

wherein $R^9$ represents hydrogen.

2. A compound of claim 1 wherein $R^2$ represents a neuraminic acid group represented by formula (V) and $R^3$ represents hydrogen.

3. A compound of claim 1 wherein $R^3$ represents a neuraminic acid group represented by formula (V) and $R^2$ represents hydrogen.

4. A compound represented by formula (II) below:

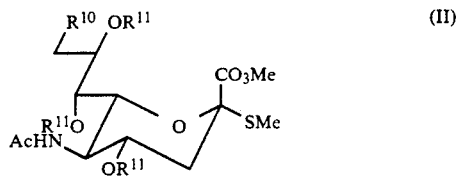

(II)

wherein $R^{10}$ represents N$_3$ or OMs and $R^{11}$ represents hydrogen or an acetyl group.

5. A compound of claim 4 wherein $R^{10}$ represents OMs and $R^{11}$ represents hydrogen.

6. A compound of claim 4 wherein $R^{10}$ represents N$_3$ and $R^{11}$ represents an acetyl group.

* * * * *